US006042812A

United States Patent [19]
Sanker et al.

[11] Patent Number: 6,042,812
[45] Date of Patent: Mar. 28, 2000

[54] FLAVOR SYSTEMS FOR ORAL CARE PRODUCTS

[75] Inventors: Lowell Alan Sanker, Cincinnati; James Grigg Upson, Springdale, both of Ohio

[73] Assignee: The Procter & Gamble Company, Cincinnati, Ohio

[21] Appl. No.: 08/756,671

[22] Filed: Nov. 26, 1996

[51] Int. Cl.⁷ .............. A61K 7/16; A61K 7/18; A61K 7/20; A61K 7/26
[52] U.S. Cl. .............. 424/49; 424/52; 424/53; 424/57; 424/58
[58] Field of Search ........................ 424/49–58

[56] References Cited

U.S. PATENT DOCUMENTS

| | | | |
|---|---|---|---|
| 3,928,560 | 12/1975 | Neely et al. | 424/52 |
| 4,011,349 | 3/1977 | Riesen | 426/540 |
| 4,085,232 | 4/1978 | Elsenstaut et al. | 426/548 |
| 4,198,394 | 4/1980 | Faunce | 424/52 |
| 4,368,213 | 1/1983 | Hollenbach et al. | 426/596 |
| 4,412,984 | 11/1983 | Van der Loo et al. | 424/58 |
| 4,532,124 | 7/1985 | Pearle | 424/52 |
| 4,770,892 | 9/1988 | Grealy et al. | 426/570 |
| 4,876,106 | 10/1989 | Sabatura | 426/583 |
| 4,911,927 | 3/1990 | Hill et al. | 424/443 |
| 4,925,655 | 5/1990 | Smigel et al. | 424/52 |
| 4,945,087 | 7/1990 | Talwar et al. | 514/60 |
| 5,011,688 | 4/1991 | Cazam et al. | 424/195.1 |
| 5,085,850 | 2/1992 | Pan et al. | 424/49 |
| 5,098,711 | 3/1992 | Hill et al. | 424/49 |
| 5,149,521 | 9/1992 | Hirose et al. | 424/58 |
| 5,165,913 | 11/1992 | Hill et al. | 424/49 |
| 5,256,402 | 10/1993 | Prencipe et al. | 424/53 |
| 5,292,502 | 3/1994 | Burke et al. | 424/54 |
| 5,296,215 | 3/1994 | Burke et al. | 424/49 |
| 5,310,563 | 5/1994 | Curtis et al. | 424/616 |
| 5,372,803 | 12/1994 | Williams et al. | 424/53 |
| 5,380,530 | 1/1995 | Hill | 424/440 |
| 5,403,578 | 4/1995 | Gordon | 424/53 |
| 5,424,059 | 6/1995 | Prencipe et al. | 424/52 |
| 5,451,401 | 9/1995 | Zerby et al. | 424/57 |
| 5,456,902 | 10/1995 | Williams et al. | 424/49 |
| 5,458,890 | 10/1995 | Williford et al. | 426/3 |
| 5,496,541 | 3/1996 | Cutler | 424/50 |
| 5,565,190 | 10/1996 | Santalucia et al. | 424/53 |
| 5,620,707 | 4/1997 | Sanker et al. | 424/489 |
| 5,628,986 | 5/1997 | Sanker et al. | |
| 5,776,437 | 7/1998 | Burgess et al. | 424/53 |

FOREIGN PATENT DOCUMENTS

| | | | |
|---|---|---|---|
| 2162812 | 5/1996 | Canada | A61K 7/20 |
| 2162821 | 5/1996 | Canada | A61K 7/20 |
| 2162885 | 5/1996 | Canada | A61K 7/20 |
| 85106 825A | 3/1987 | China . | |
| 0 712 624 A2 | 5/1996 | European Pat. Off. | A61K 7/16 |
| 2 240 352 | 2/1974 | Germany | A61K 7/18 |
| 64835 A2 | 3/1994 | Hungary | A61K 31/045 |
| 57-082308A2 | 5/1982 | Japan . | |
| 59-175410 A2 | 10/1984 | Japan | A61K 7/16 |
| 59-175422 A2 | 10/1984 | Japan | A61K 31/045 |
| 62-198611 A2 | 9/1987 | Japan . | |
| 05140106 A2 | 6/1993 | Japan | A61K 7/22 |
| 5-140106 A2 | 6/1993 | Japan . | |
| 8-310 930 A2 | 11/1996 | Japan . | |
| 2079325 | 1/1996 | Spain | A61K 7/28 |
| 1303162A1 | 4/1987 | U.S.S.R. . | |
| 95 07683 A1 | 3/1995 | WIPO . | |
| 95 08979A1 | 4/1995 | WIPO . | |
| WO 96/15770 | 5/1996 | WIPO | A61K 7/22 |

OTHER PUBLICATIONS

Jacobs (I) "How to Flavor Tooth Paste" American Perfumer Essential Oil Review 61:389 391–393 May 1953.
Jacobs (II) "Flavoring Mouthwashes" American Perfumer Essential Oil Review 61:469–471 Jun. 1953.
Arctander, Perfume and Flavor Chemicals, vols. 1–2 (1969), entries of relevant flavors.
Fenaroli's Handbook of Flavor Ingredients, Third Edition, vols. 1 & 2, CRC Press Inc. (1995), entries of relevant flavors.
U.S. application No. 08/334,635, Huetter, filed Nov. 4, 1994.
U.S. application No. 08/365,975, Huetter, filed Dec. 28, 1994.
U.S. application No. 08/756,450, Burgess et al., filed Nov. 26, 1996.
U.S. application No. 08/756,740, Burgess et al., filed Nov. 26, 1996.
U.S. application No. 08/756,995, Burgess et al., filed Nov. 26, 1996.
U.S. application No. 08/756,015, Burgess et al., filed Nov. 26, 1996.

*Primary Examiner*—Shep K. Rose
*Attorney, Agent, or Firm*—Angela Marie Stone; Betty J. Zea

[57] ABSTRACT

Disclosed are oral compositions comprising a total flavor system and one or more aqueous carriers, wherein the oral composition is a dentifrice or a mouthrinse. The total flavor system comprises a traditional oral care flavor system and a dairy-creme component.

14 Claims, No Drawings

FLAVOR SYSTEMS FOR ORAL CARE PRODUCTS

BACKGROUND OF THE INVENTION

In recent years, the dentifrice products have been developed to include tartar control agents, baking soda, peroxides, and antibacterial agents. Although each of these ingredients brings an added benefit to the dentifrice, it may also cause negative aesthetics, particularly taste. Despite these many advances in dentifrice formulations in recent years, there is still a need a for improved products and products with improved aesthetics and taste. The present inventors have discovered an improved flavor system comprising a traditional oral care flavor system combined with a dairy-creme component.

It is an object of the present invention to provide an oral care composition comprising a flavor system which is consumer preferred. A further object of the present invention is to provide compositions which deliver a variety of benefits to the mouth, such as those described above, and improved taste.

These and other objects of the present invention will become readily apparent from the detailed description which follows.

All percentages and ratios used herein are by weight of the total composition, and all measurements are made at 25° C., unless otherwise specified.

SUMMARY OF THE INVENTION

An oral composition comprising from about 0.1% to about 10% of a total flavor system and from about 90% to about 99.9% of one or more aqueous carriers, wherein the oral composition is a dentifrice or a mouthrinse. The total flavor system comprises, by weight of the total flavor system, from about 50% to about 99.5% of a traditional oral care flavor system and from about 0.5% to about 50% of a dairy-creme component.

DETAILED DESCRIPTION OF THE INVENTION

The oral compositions of the present invention may be in the form of a toothpaste, mouth rinse, or liquid dentifrice. The term "toothpaste", as used herein, means paste or gel formulations unless otherwise specified. The toothpaste may also be a multilayer composition which is extruded from the tube in combination paste/gel stripes. One of the layers must comprise all of the essential components, while the other layers may contain less than all of the essential components or may be any dentifrice formulation.

The term "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the compositions of the present invention. Such materials include fluoride ion sources, pyrophosphate source, peroxide source, alkali metal bicarbonate salt, xylitol, thickening materials, humectants, water, buffering agents, abrasive polishing materials, surfactants, titanium dioxide, sweetening agents, coloring agents, and mixtures thereof.

The present compositions comprise essential components, as well as optional components. The essential and optional components of the compositions of the present invention are described in the following paragraphs.

TOTAL FLAVOR SYSTEM

The present composition includes a total flavor system. The "total flavor system", as used herein, means all of the flavor systems or components added to the oral care composition. This total flavor system comprises a traditional oral care flavor system and a dairy-creme component. The total flavor system may optionally comprise a coolant. The components of the total flavor system may be in the form of an oil, liquid, semi-solid, solid, or powder. The components of the total flavor system may be of a natural and/or synthetic flavor origin.

The total flavor system is used in the present composition at levels of from about 0.1% to about 10%, preferably from about 0.5% to about 5%, and most preferably from about 0.8% to about 2%, by weight of the composition.

Traditional Oral Care Flavor System

Various flavors can be used in the total flavor system of the present invention. The term "traditional oral care flavor system", as used herein, means any flavor system comprising flavor components suitable for use in oral care products. The traditional oral care flavor system generally consists of flavor components from the group consisting of peppermint, spearmint, cinnamon, spice, wintergreen, fruit, citrus, herbal, medicinal, and common food flavors (i.e. chocolate) and mixtures thereof. Illustrative, but nonlimiting examples of such traditional oral care flavor system components include peppermint oils such as *Mentha piperita* and *Mentha arvensis*; spearmint oils such as *Mentha cardiaca* and *Mentha spicata*; hydrocarbons such as limonene, caryophyllene, myrcene, and humulene; alcohols such as menthol, linalool, 3-decanol, and pinocarveol; ketones such as peperitone, menthone, spicatone, and 1-carvone; aldehydes such as acetaldehyde, 3-hexanal, or n-octanal; oxides such as menthofuran, pepertione oxide, or carvyl acetate-7,7 oxide; acids such as acetic and ocenoic; and sulphides such as dimethyl sulphide. Flavor system components also include esters such as menthyl acetate, benzyl isobutyrate, and 3-octyl acetate. The esters are stable in compositions having a pH of about 7 or lower, and preferably a pH of about 4.5 or lower. The traditional oral care flavor components may also consist of essential oils such sage oil, parsley oil, marjoram oil, cassia oil, clove bud oil, cinnamon oil, eucalyptus oil, anise oil, and mixtures thereof. The traditional oral care flavor components may also consist of flavor chemicals such as cinnamic aldehyde, eugenol, ionone, anethole, eucalyptol, methyl salicylate, oxanone, alpha-irisone, and mixtures thereof. Preferred are peppermint oils, spearmint oils, menthol, anethole, methyl salicylate, cinnamon oils, clove bud oils, oxanone, and mixtures thereof. Flavor components are described in more detail in Fenaroli's *Handbook of Flavor Ingredients*, Third Edition, Volumes 1 & 2, CRC Press, Inc. (1995), and Steffen Arctander's *Perfume and Flavor Chemicals*, Volumes 1 & 2, (1969). Traditional oral care flavor systems are used at levels of from about 50% to about 99.5%, preferably from about 75% to about 99%, and more preferably from about 95% to about 99%, by weight of the total flavor system.

Dairy-Creme Component

The total flavor system additionally comprises a dairy-creme component. The term "dairy-creme component", as used herein, means any material suitable for use as a flavor component providing a vanilla-like flavor with a dairy note. Illustrative but nonlimiting examples of such dairy-creme components include vanillin, ethyl vanillin, heliotropine, propenyl guaethol, vanilla extracts, veratraldehyde, 4-cisheptenal, diacetyl, butyl lactate, ethyl lactate, methyl-para-tert-butyl phenyl acetate, gamma and delta hexalactone and heptalactone, benzodihydropyrone, butter starter distillate, delta tetradecalactone, butyraldehyde, and mixtures thereof. Preferred are vanillin, ethyl vanillin, heliotropine, 4-cis-heptenal, diacetyl, and methyl-para-tert-butyl phenyl acetate. It is preferred that the dairy-creme component comprise a minimal amount of solvent or diluent. Common solvents or diluents include propylene glycol, neobee, and others commonly used in the flavor industry. The diluted dairy-creme components may be used in the flavor system. Dairy-creme components are used at levels of from about 0.5% to about 50%, preferably 1% to about 25%, and more preferably from about 1% to about 5%, by weight of the total flavor system. The amounts given are for the concentrated flavor component and do not include excess amounts, 40% or more, of a solvent or diluent.

A coolant may also be incorporate into the total flavor system. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, (known commercially as "WS-3") and mixtures thereof. The coolant may be present at an amount of from about 0% to about 25% and preferably from about 4% to about 10%, by weight of the total flavor system.

AQUEOUS CARRIERS

In preparing the present compositions, it is desirable to add one or more aqueous carriers to the compositions. Aqueous carriers contain materials that are well known in the art and readily chosen by one skilled in the art based on the physical and aesthetic properties desired for the compositions being prepared. Aqueous carriers typically comprise from about 90% to about 99.9%, preferably from about 95% to about 99.5%, and more preferably from about 98% to about 99.2%, by weight of the total composition.

Fluoride Ion Source

The present invention incorporates a soluble fluoride source capable of providing free fluoride ions. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

The present compositions contain a soluble fluoride source capable of providing from about 50 ppm to about 3500 ppm, and preferably from about 500 ppm to about 3000 ppm of free fluoride ions.

Pyrophosphate Source

The present invention may also include a pyrophosphate ion source which is from a pyrophosphate salt. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the total composition. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the composition. Some or all of the tetrasodium pyrophosphate is undissolved in the product and is present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such known materials as synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Peroxide Source

The present invention may include a peroxide source. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the total composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 50%, preferably from about 0.5% to about 30%, more preferably from about 0.5% to about 15%, and most preferably from about 0.8% to about 2% of an alkali metal bicarbonate salt, by weight of the total composition.

Xylitol

The present invention may also include xylitol. Xylitol is a sugar alcohol that is used as a sweetener or humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition.

Additional Aqueous Carriers

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the total composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. Polyethylene glycols are one of the preferred humectants. Polyethylene glycols useful herein are those which are liquids at room temperature or have a melting point slightly there above. Liquid and low-melting polyethylene glycols are commercially available from Union Carbide under the Carbowax® tradename. Preferred are those polyethylene glycols having a molecular weight range of from about 200 to about 2000 and corresponding n values of from about 4 to about 40. More preferred are polyethylene glycols having a molecular weight range of from about 400 to about 1600. The humectant generally comprises from about 0% to 70%, and preferably from about 15% to 55%, by weight of the compositions herein.

Water employed in the preparation of commercially suitable oral compositions should preferably be of low ion content and free of organic impurities. Water generally comprises from about 5% to about 70%, and preferably from about 20% to about 50%, by weight of the composition herein. Some compositions may comprise a low level of water, generally from about 5% to about 20% and preferably from about 9% to about 14%, more preferably from about 9.1% to about 12%, and most preferably from about 10% to about 11%. The amounts of water include the free water which is added plus that which is introduced with other materials, such as with sorbitol, silica, surfactant solutions, and/or color solutions.

The pH of the present compositions is preferably adjusted through the use of buffering agents. Buffering agents, as used herein, refer to agents that can be used to adjust the pH of the compositions to a range of about pH 6.5 to about pH 10.5. The compositions may contain a high pH range of from about 9.0 to about 10.5. These agents include monosodium phosphate, trisodium phosphate, sodium hydroxide, sodium carbonate, citric acid, and sodium citrate. Buffering agents can be used at a level of from about 0.5% to about 10%, by weight of the present compositions.

An abrasive polishing material may also be included in the toothpaste compositions. The abrasive polishing material contemplated for use in the compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. The abrasive in the toothpaste compositions described herein is generally present at a level of from about 6% to about 70% by weight of the composition. Preferably, toothpastes contain from about 10% to about 50% of abrasive, by weight of the composition.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the compositions.

Coloring agents may also be added to the present composition. The coloring agent may be in the form of an aqueous solution, preferably 1% coloring agent in a solution of water. Color solutions generally comprise from about 0.01% to about 5%, by weight of the composition.

Sweetening agents can be added to the compositions. These include sodium saccharin, dextrose, sucrose, chlorinated sucrose, lactose, maltose, levulose, aspartame, sodium cyclamate, D-tryptophan, dihydrochalcones, acesulfame, monoammonium glycyrrhizinate, and mixtures thereof. Sweetening agents are generally used in toothpastes at levels of from about 0.005% to about 5%, by weight of the composition.

The present invention may also include other agents. Included among such agents are water insoluble non-cationic agents such as triclosan and other agents of the type disclosed in Parran, Jr. et al., U.S. Pat. No. 5,015,466, issued May 14, 1991, incorporated by reference herein in its entirety.

The composition can be in the form of a multilayer toothpaste composition. This composition may comprise two or more separate layers which are in contact with each other. Preferably, the separate layers are a paste and a gel that when extruded from the tube, appear as combination paste/gel stripes. One of the layers must comprise all of the essential components, while the other layers may contain less than all of the essential components or may be any dentifrice formulation.

Alternatively, the dentifrice compositions may be physically separated in a dentifrice dispenser. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

The present compositions can be in the form of a mouth rinse or liquid dentifrice where conventional mouth rinse components comprise the aqueous carriers of the present invention. Mouth rinses and liquid dentifrices generally comprise from about 20:1 to about 2:1 of a water ethyl alcohol or alcohol free solution, and preferably other ingredients such as flavors, sweeteners, and humectants as those mentioned above. The humectants, such as glycerin and sorbitol, give a moist feel to the mouth. Generally on a weight basis, the mouth rinses and liquid dentifrices of the present invention comprise from about 0% to about 60% ethyl alcohol, from about 0% to about 20% humectant, from about 0% to about 0.5% sweetening agent, from about 0% to about 0.3% of a flavoring system, and the balance water. Other optional components described herein for use in toothpaste products are also useful in the mouth rinse and liquid dentifrice compositions.

Method of Manufacturing

Toothpaste compositions of the present invention are prepared by mixing together the components described above. If the present composition does not contain a pyrophosphate salt or contains predominately dissolved pyrophosphate salt, the method of manufacturing comprises conventional toothpaste manufacturing methods. A typical method is described after Examples I, II, and III.

If the present composition contains predominately undissolved pyrophosphate salt, the method of manufacturing comprises the steps of: (a) preparing a mixture of one or more aqueous carrier materials; (b) adding tetrasodium pyrophosphate, all at once or in portions, under conditions whereby less than about 20% of the total pyrophosphate is dissolved in the dentifrice mixture; and wherein further any remaining aqueous carrier materials not added to the mixture during step (a) are added in whole or in part in step (b) or thereafter, either by themselves or with any remaining amount of the tetrasodium pyrophosphate, under conditions such that less than about 20% of the total pyrophosphate is dissolved in the mixture. Preferably, the amount of pyrophosphate dissolved in the mixture for the methods and compositions of the present invention is less than about 10% by weight of the total pyrophosphate present in the compositions.

Preferably, one or more of the following process conditions are controlled as follows to limit the solubility of the tetrasodium pyrophosphate in the dentifrice mixture: (1) the neat (undiluted) pH of the process mixture is above about pH 8 during and after the tetrasodium pyrophosphate addition to the mixture; (2) the tetrasodium pyrophosphate salt is one of the last components to be added to the process mixture, preferably after all or much of the other sodium-containing salts present in the composition have been added to the process mixture; and (3) after the tetrasodium pyrophosphate salt is added, the temperature of the mixture is heated to a temperature range of from about 38° C., to about 71° C.

By this method, the composition will have less than about 20% of the total pyrophosphate dissolved in the dentifrice composition and the dissolved tetrasodium pyrophosphate salt is less likely to recrystalize in the form of glass-like crystal particles of tetrasodium pyrophosphate decahydrate.

After the toothpaste is made, it is fed into a suitable dispensing tube or container. After filling the tube with toothpaste, the open end of the tube is sealed. If the toothpaste is to be a multilayer composition, the desired toothpaste layers are fed in parallel streams to form a multilayered appearance and then the open end of the tube is sealed. The dentifrice layers will be extruded in the desired multilayer configuration when dispensed from the tube.

Method of Treatment

The present invention compositions additionally relate to a method for reducing plaque on dental enamel. The method of treatment herein comprises contacting the dental enamel surfaces in the mouth with the oral compositions according to the present invention.

The following examples further describe and demonstrate embodiments within the scope of the present invention. These examples are given solely for the purpose of illustration and are not to be construed as limitations of the present invention as many variations thereof are possible without departing from the spirit and scope.

EXAMPLE I

| Ingredient | Weight % |
| --- | --- |
| Sorbitol[a] | 48.767 |
| Glycerin | 10.000 |
| Water | 12.340 |
| Sodium Fluoride | 0.243 |
| Sodium Saccharin | 0.400 |
| Monosodium Phosphate | 0.500 |
| Trisodium Phosphate | 1.500 |
| Xanthan Gum | 0.400 |
| Carbopol | 0.300 |
| Titanium Dioxide | 0.500 |
| Color Solution | 0.050 |
| Silica | 20.000 |
| Sodium Alkyl Sulfate[c] | 4.000 |
| Flavor System | 1.000 |

| Flavor System | Weight % of Flavor System |
| --- | --- |
| Peppermint | 64.000 |
| Anethole | 10.000 |
| Dairy-creme Flavor | 5.000 |
| Cinnamon Oil | 8.000 |
| Clove Bud Oil | 8.000 |
| Coolant | 5.000 |

Example I is prepared as follows. Start by combining water and sorbitol. Mix thoroughly and add sodium fluoride, saccharin, and the phosphates. Next add the silica. Disperse the thickening agents, xanthan gum and carbopol, in the remaining humectant, glycerin, before adding to the mixture. Lastly, add the flavor system, color solution, titanium dioxide, and surfactant, sodium alkyl sulfate. Continue mixing until homogeneous. Mill and/or deareate the final product if desired for aesthetic preference.

EXAMPLE II

| Ingredient | Weight % |
| --- | --- |
| Sorbitol[a] | 36.240 |
| Glycerin | 10.000 |
| Water | 10.217 |
| Sodium Fluoride | 0.243 |
| Sodium Saccharin | 0.500 |
| Sodium Carbonate | 1.500 |
| Sodium Bicarbonate | 24.000 |
| Carboxymethylcellulose | 1.000 |
| Titanium Dioxide | 0.500 |
| Silica | 11.000 |
| Sodium Alkyl Sulfate[c] | 4.000 |
| Flavor System | 0.800 |

| Flavor System | Weight % of Flavor System |
| --- | --- |
| Peppermint | 10.000 |
| Spearmint Oil | 45.000 |
| Menthol | 25.000 |
| Anethole | 10.000 |
| Dairy-creme Flavor | 5.000 |
| Coolant | 5.000 |

Example II is prepared as follows. Start by combining water and sorbitol. Mix thoroughly and add sodium fluoride and saccharin. Next add the sodium carbonate, sodium bicarbonate, and then the silica. Disperse the thickening agents, carboxymethylcellulose, in the remaining humectant, glycerin, before adding to the mixture. Lastly, add the flavor system, titanium dioxide, and surfactant, sodium alkyl sulfate. Continue mixing until homogeneous. Mill and/or deareate the final product if desired for aesthetic preference.

EXAMPLE III

| Ingredient | Weight % |
| --- | --- |
| Sorbitol[a] | 23.904 |
| Glycerin | 8.501 |
| Water | 23.511 |
| Sodium Fluoride | 0.243 |
| Sodium Saccharin | 0.500 |
| Sodium Acid Pyrophosphate | 2.500 |
| Tetrasodium Pyrophosphate | 0.758 |
| Propylene Glycol 6 | 3.000 |
| Tetrapotassium Pyrophosphate[b] | 7.783 |
| Xanthan Gum | 0.450 |
| Carbopol | 0.300 |
| Titanium Dioxide | 0.500 |
| Color Solution | 0.050 |
| Silica | 22.000 |
| Sodium Alkyl Sulfate[c] | 4.000 |
| Flavor System | 2.000 |

| Flavor System | Weight % of Flavor System |
| --- | --- |
| Peppermint | 5.000 |
| Menthol | 30.000 |
| Anethole | 3.000 |
| Dairy-creme Flavor | 2.000 |
| Orange Oil | 30.000 |
| Oxanone | 1.000 |
| Lemon Oil | 20.000 |
| WS-3 Coolant | 6.000 |
| Coolant | 3.000 |

Example III is prepared as follows. Start by combining water and sorbitol. Mix thoroughly and add sodium fluoride and saccharin. In the order listed, add sodium acid pyrophosphate, tetrasodium pyrophosphate, and tetrapotassium pyrophosphate. Next add the silica. Disperse the thickening agents, xanthan gum and carbopol, in the glycerin, before adding to the mixture. Add the polyethylene glycol. Lastly, add the flavor system, color solution, and surfactant, sodium alkyl sulfate. Continue mixing until homogeneous. Mill and/or deareate the final product if desired for aesthetic preference.

EXAMPLE IV

| Ingredient | Weight % |
|---|---|
| Sorbitol[a] | 13.611 |
| Glycerin | 15.000 |
| Water | 19.473 |
| Sodium Fluoride | 0.243 |
| Sodium Saccharin | 0.528 |
| Tetrasodium Pyrophosphate | 5.045 |
| Propylene Glycol 6 | 3.000 |
| Sodium Carbonate | 1.500 |
| Sodium Bicarbonate | 24.000 |
| Carboxymethylcellulose | 0.800 |
| Color Solution | 0.300 |
| Silica | 11.000 |
| Sodium Alkyl Sulfate[c] | 4.000 |
| Flavor System | 1.500 |

| Flavor System | Weight % of Flavor System |
|---|---|
| Peppermint | 30.000 |
| Spearmint Oil | 30.000 |
| Menthol | 25.000 |
| Anethole | 10.000 |
| Dairy-creme Flavor | 5.000 |

Example IV is prepared as follows. Start by combining water and sorbitol. Add sodium fluoride and saccharin. Add sodium carbonate. Next add the silica. The temperature of the mixture should be about 32° C. or less prior to the addition of sodium bicarbonate. Next, disperse the thickening agent, carboxymethylcellulose, in the glycerin, before adding to the mixture. Add the polyethylene glycol. Next add the flavor system, color solution, and surfactant, sodium alkyl sulfate. Lastly, slowly add the tetrasodium pyrophosphate. Continue mixing until homogeneous. Mill and/or deareate the final product if desired for aesthetic preference.

EXAMPLE V

| Ingredient | Weight % |
|---|---|
| Xylitol | 5.000 |
| Water | 26.500 |
| Saccharin | 0.400 |
| Sodium Fluoride | 0.243 |
| Glycerin | 23.561 |
| Polyethylene Glycol | 1.000 |
| Carboxymethylcellulose | 0.250 |
| Xanthan Gum | 0.600 |
| Sodium Bicarbonate | 2.500 |
| Sodium Carbonate | 1.250 |
| Tetrasodium pyrophosphate | 5.046 |
| Silica | 25.000 |
| Titanium Dioxide | 0.750 |
| Sodium alkyl sulfate[c] | 5.000 |
| Poloxamer 407 | 2.000 |
| Flavor System | 0.900 |

| Flavor System | Weight % of Flavor System |
|---|---|
| Peppermint | 55.000 |
| Spearmint Oil | 2.000 |
| Menthol | 20.000 |
| Anethole | 14.000 |
| Dairy-creme Flavor | 1.000 |
| Coolant | 8.000 |

Example V is prepared as follows. Start by combining water and enough glycerin to provide sufficient liquid for adequate mixing. Add xylitol and poloxamer to the mixture. Mix thoroughly and add sodium fluoride and saccharin. Add sodium carbonate. Next add the silica. The temperature of the mixture should be about 32° C. or less prior to the addition of sodium bicarbonate. Next, disperse the thickening agents, carboxymethylcellulose and xanthan gum, in the remaining glycerin, before adding to the mixture. Add the polyethylene glycol. Next add the flavor system, titanium dioxide, and surfactant, sodium alkyl sulfate. Lastly, slowly add the tetrasodium pyrophosphate. Continue mixing until homogeneous. Mill and/or deareate the final product if desired for aesthetic preference.

EXAMPLE VI

| Ingredient | Weight % |
|---|---|
| Glycerin | 27.050 |
| Polyethylene Glycol 12 | 2.000 |
| Xanthan Gum | 0.300 |
| Carboxymethylcellulose | 0.200 |
| Water | 5.000 |
| Sodium Saccharin | 0.450 |
| Sodium Fluoride | 0.243 |
| Xylitol | 10.000 |
| Poloxamer 407 | 2.000 |
| Sodium Alkyl Sulfate[c] | 6.000 |
| Sodium Carbonate | 2.600 |
| Titanium Dioxide | 1.000 |
| Silica | 20.000 |
| Sodium Bicarbonate | 1.500 |
| Propylene Glycol | 15.011 |
| Tetrasodium Pyrophosphate | 5.046 |
| Calcium Peroxide | 0.500 |
| Flavor System | 1.100 |

| Flavor System | Weight % of Flavor System |
|---|---|
| Peppermint | 55.000 |
| Spearmint Oil | 2.000 |
| Menthol | 20.000 |
| Anethole | 12.500 |
| Dairy-creme Flavor | 2.500 |
| WS-3 Coolant | 8.000 |

[a] 70% solution of sorbitol in water
[b] 60% solution of tetrapotassium pyrophosphate in water
[c] 27.9% solution of sodium alkyl sulfate in water Example VI is prepared as follows: Add approximately half of the glycerin to a mixing vessel. Disperse the thickening agents, carboxymethyl cellulose and xanthan gum, in the polypropylene glycol. Add this mixture to the mixing vessel, then add the polyethylene glycol. Dissolve the sodium fluoride and sodium saccharin in water and add to the mixture. Add the xylitol and poloxamer. The flavor system and sodium alkyl sulfate are then added. Next, add the sodium carbonate, titanium dioxide, and the silica. Add the sodium bicarbonate. Disperse the tetrasodium pyrophosphate in the remaining glycerin and add to the mixture. Finally, add the calcium peroxide. Stir the mixture until homogeneous and then heat the mixture to a temperature range of from about 110° F. to about 160° F. This temperature should be maintained for about 30–60 minutes. Finally, the mixture may be cooled and deaerated.

What is claimed is:

1. An oral composition comprising:
   a. from about 0.1% to about 10% of a total flavor system which comprises from about 50% to about 99.5% of a traditional oral care flavor system wherein components of the traditional oral care flavor system are selected from the group consisting of natural and/or synthetic peppermint oil and spearmint oil, menthol, anethole, methyl salicylate, cinnamon oil, clove bud oil, oxanone, and mixtures thereof, and from about 0.5% to about 50% of a dairy-creme component wherein the dairy-creme component is selected from the group consisting of vanillin, ethyl vanillin, heliotropine, 4-cis-heptanal, diacetyl, and methyl-para-tert-butyl phenyl acetate, and mixtures thereof, by weight of the total flavor system;
   b. a soluble fluoride source capable of providing from about 50 to about 3500 ppm of free fluoride ions; and
   c. from about 90% to about 99.9% of one or more aqueous toothpaste, gel or liquid dentifrice, or mouthrinse carriers;
   wherein the oral composition is a dentifrice containing at least one negative aesthetic or unpleasant taste resulting from a polyphosphate, pyrophosphate, tripolyphosphate, hexamethaphosphate, or zinc citrate tartar control agent, baking, soda, peroxide, and/or mixtures thereof, said total flavor system being effective to improve said negative aesthetic or unpleasant taste.

2. The oral composition according to claim 1 wherein the traditional oral care flavor system is from about 75% to about 99% of the total flavor system.

3. The oral composition according to claim 2 wherein the dairy-creme component is in an amount of from about 1% to about 25% of the total flavor system.

4. The oral composition according to claim 3 wherein the total flavor system further comprises from about 0% to about 25% of a coolant by weight of the total flavor system.

5. The oral composition according to claim 3 wherein the soluble fluoride source is sodium fluoride.

6. The oral composition according to claim 5 further comprising an amount of at least one pyrophosphate ion source sufficient to provide at least about 1.5% free pyrophosphate ions.

7. The oral composition according to claim 6 further comprising from about 0.5% to about 50% of an alkali metal bicarbonate salt.

8. The oral composition according to claim 7 further comprising from about 0.01% to about 10% of a peroxide source.

9. The oral composition according to claim 8 further comprising from about 0.01% to about 25% of xylitol.

10. The oral composition according to claim 9 further comprising one or more surfactants each at a level of from about 0.25% to about 12.0%.

11. The oral composition according to claim 10 having a pH in a range of from about 6.5 to about 10.5.

12. The oral composition according to claim 11 wherein the aqueous carriers are materials selected from the group consisting of thickening materials, humectants, water, buffering agents, abrasive polishing materials, titanium dioxide, sweetening agents, coloring agents, and mixtures thereof.

13. The oral composition according to claim 12 wherein the composition is a multilayer composition which is extruded from a tube in combination paste/gel stripes.

14. An oral composition comprising:
   a. from about 0.1% to about 10% of a total flavor system which comprises from about 50% to about 99.5% of a traditional oral care flavor system wherein components of the traditional oral care flavor system are selected from the group consisting of natural and/or synthetic peppermint oil and spearmint oil, menthol, anethole, methyl salicylate, cinnamon oil, clove bud oil, oxanone, and mixtures thereof, and from about 0.5% to about 50% of a dairy-creme component wherein the dairy-creme component is selected from the group consisting of vanillin, ethyl vanillin, heliotropine, 4cis-heptanal, diacetyl, and methyl-para-tert-butyl phenyl acetate, and mixtures thereof, by weight of the total flavor system;
   b. a soluble fluoride source capable of providing from about 50 to about 3500 ppm of free fluoride ions;
   c. an amount of at least about 1.5% tetrasodium pyrophosphate;
   d. from about 0.1% to about 5% of calcium peroxide; and
   e. from about 85% to about 98% of one or more aqueous toothpaste, gel or liquid dentifrice, or mouthrinse carriers;
   wherein the oral composition is a dentifrice, wherein said total flavor system is effective to improve a negative aesthetic or unpleasant taste resulting from the tetrasodium pyroaphosphate and/or the calcium peroxide.

* * * * *